(12) United States Patent
Caires et al.

(10) Patent No.: US 8,212,090 B2
(45) Date of Patent: Jul. 3, 2012

(54) METHODS FOR SILVER-PROMOTED FLUORINATION OF ORGANIC MOLECULES

(75) Inventors: Christopher C. Caires, Menlo Park, CA (US); Samira Guccione, Hillsborough, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 343 days.

(21) Appl. No.: 12/634,816

(22) Filed: Dec. 10, 2009

(65) Prior Publication Data

US 2010/0152502 A1    Jun. 17, 2010

Related U.S. Application Data

(60) Provisional application No. 61/121,708, filed on Dec. 11, 2008.

(51) Int. Cl.
*C07C 22/00* (2006.01)

(52) U.S. Cl. ...................................................... 570/147

(58) Field of Classification Search .................. None
See application file for complete search history.

(56) References Cited

U.S. PATENT DOCUMENTS 5,315,043 A * 5/1994 Fernandez et al. ............ 568/932
7,202,388 B2 * 4/2007 Grushin ......................... 570/147

OTHER PUBLICATIONS

Pogany et al., Synthesis (1987) 718).
Taylor et al., (1977) J. Org. Chem. 42: 362-363.
Grushnin V.V. (2000) Organometallics 19: 1888-1900.
Fraser et al., (1997) J. Am. Chem. Soc. 119: 4769-4770.
Barthazy et al., (2000) Organometallics 19: 2844-2852.
Barthazy et al., Organometallics (2001) 20: 3472-3477).
Tannhauser et al., J. Am. Chem. Soc. (1956) 78: 2658-2659.

* cited by examiner

*Primary Examiner* — Sudhakar Katakam
(74) *Attorney, Agent, or Firm* — Thomas, Kayden, Horstemeyer & Risley, LLP

(57) ABSTRACT

The methods of the disclosure may be used for the fluorination of organic compounds, and in particular aryl organic compounds other than just benzyl halogens. It is within the scope of the present disclosure, for organic compounds comprising an electrophilic carbon atom and a halogen leaving group to be fluorinated by the methods of the disclosure. One aspect of the disclosure provides methods of introducing a fluorine atom onto an electrophilic carbon atom, comprising mixing an insoluble basic silver salt, an organic molecule containing a leaving group, an aqueous solution of hydrofluoric acid, and a polar solvent:water composition; incubating said mixture at a temperature of about 20° C. to about 35° C., thereby obtaining a fluorinated organic product.

6 Claims, No Drawings

METHODS FOR SILVER-PROMOTED FLUORINATION OF ORGANIC MOLECULES

CROSS-REFERENCE TO RELATED APPLICATIONS

This application claims priority to U.S. Provisional Patent Application Ser. No. 61/121,708, entitled "METHODS FOR SILVER PROMOTED FLUORINATION OF ORGANIC MOLECULES" filed on Dec. 11, 2008, the entirety of which is hereby incorporated by reference.

TECHNICAL FIELD

The present disclosure is generally related to methods of fluoridating an organic compound promoted by silver compounds under mild conditions.

BACKGROUND

The Balz-Schiemann reaction is still considered the most reliable and useful method of making aryl C—F bonds (Balz & Schiemann, G. *Ber. Dtsch. Chem. Ges.* (1927) 60: 1186). While most fluoride displacements on an aromatic ring require the presence of an electron withdrawing group, the Balz-Schiemann reaction performs well for both electron-rich and electron-deficient rings, making it more reliable then any other displacement method. The mechanism of the reaction starts with loss of $N_{2(g)}$ to form a phenyl cation. The phenyl cation then abstracts a fluoride from the counterion, resulting in fluorobenzene and $BF_3$. The phenyl cation intermediate is also invoked for similar reactions where the leaving group can be either iodobenzene, Pb(II), or Tl(I).

The use of organothallium(III) salts to make Ar—F bonds was one of the first methods discovered that rivaled the original Balz-Schiemann reaction (Taylor et al., (1977) *J. Org. Chem.* 42: 362-363). By treating simple aromatics with thallium (III) trifluoroacetate the desired aryl thallium species could be obtained in good yield. Ligand exchange of aryl thallium compounds with potassium fluoride easily gave the desired ArylTlF$_2$.

Initial attempts involved thermally heating (4-ethylbenzene) TlF$_2$ to 250-300° C., which only gave ethyl benzene in 41% yield as the product. Photolysis of the same substrate with UV light gave no reaction and recovery of starting material. Under similar conditions UV photolysis of arylthallium (III) cyanides or isothiocyanates gave ArCN and ArSCN. Similarly, arylthallium (III) bromides and iodines decompose spontaneously at or slightly above room temperature to give ArBr, and ArI. The desired aryl fluorides, however, were only finally obtained by refluxing the arylthallium (III) difluoride in cyclohexane saturated with BF$_3$ for 2 hours. The mechanism is presumed to be in situ formation of ArTl(BF$_4$)$_2$ followed by a Balz-Schiemann type process.

Aryl plumbanes, like aryl thallanes, also readily decompose in the presence of BF$_3$ to form ArF bonds in good yield (Taylor et al., *J. Org. Chem.* (1977, 42: 362-363)). The starting aryllead(IV) triacetate can be prepared by either trans-metalation from the aryl silane, stannane, or boronic acid with Pb(OAc)$_4$ or directly via electrophilic aromatic substitution with Pb(OAc)$_4$ and a catalytic amount of Hg(OAc)$_2$. Stirring the aryllead(IV) triacetate in BF$_3$.OEt$_2$ (as the solvent) at room temperature overnight afforded the desired aryl fluoride in generally good yield. The proposed mechanism is similar to the Balz-Schiemann mechanism and is supported by two results. The first, when p-tolyllead(IV) triacetate was stirred with BF$_3$.OEt$_2$ and a large excess of benzene the product mixture is: 4-methylbiphenyl 8%; p-tolyl acetate 5%; and p-flurotoluene (33%). Switching the benzene co-solvent to mesitylene gave: 2,4,4,6-tetramethylbiphenyl 5%; p-tolyl acetate 5%; p-fluorotoluene 19%.

On heating bis(triphenylphosphine)palladium(fluoro)phenyl in toluene it was found that the desired reductive elimination to form PhF did not occur, but instead a variety of oxidized products were formed (Grushnin V. V. (2009) *Organometallics* 19: 1880-1900). Two pathways were proposed: first, α-elimination of a phenyl group to make the transient palladium(IV) species, followed by reductive elimination to form biphenyl. Ligand metathesis generates the L$_n$PdF$_2$ species which eliminates to form triphenylphosphane difluoride; and, second, reductive elimination to form a fluorophosphonium cation (tight ion pair) followed by oxidative addition into the P—C bond to give the Pd(II) biphenyl species. From here reductive elimination occurs to form biphenyl and the resulting intermediate enters into the first pathway. Exposure of (PPh$_3$)$_2$Pd(X)(Ph) to CO when X=Cl, Br or I results in the formation of stable CO inserted products (PPh$_3$)$_2$Pd(X)(COPh) (Fraser et al., (1997) *J. Am. Chem. Soc.* 119: 4769-4770; Grushnin et al., (1997) *J. Am. Chem. Soc.* 119:4769-4770). However, when X=F the product immediately reductively eliminates to form the corresponding acyl fluoride. This result represents the only reductive elimination from a palladium (II) center to make a C—F bond.

Unlike Pd(II), Pd(IV) species have been shown to be useful for forming C—F bonds. It has been shown that directed cyclopalladated Pd(II) species, when treated with an electrophilic fluorine source, cleanly converted to the desired aryl or alkyl fluoride The reaction of cationic Ru(II) fluorides to promote halide displace on electron rich C—H bonds has been studied (Mazetti et al., (2000) *Organometallics* 19: 2844-2852). Treatment of [(dppp)$_2$RuF]$^+$ with secondary or tertiary chlorides and bromides affords the desired alkyl fluorides in high yield (Barthazy et al., (2000) *Organometallics* 19: 2844-2852. Aryl substitution on the electrophilic center favors the reaction, and primary systems decomposed to unidentifiable products. A catalytic version of this reaction using thallium (I) fluoride as the stoichiometric fluoride source was also developed (Barthazy et al., *Organometallics* (2001) 20: 3472-3477).

SUMMARY

Briefly described, embodiments of this disclosure, among others, encompass methods for the making of C—F bonds using anionic fluoride and which would be advantageous for radiochemical synthesis. In the methods of the disclosure, embodiments of the reactions of the disclosure use silver oxide and HF$_{(aq)}$ for the synthesis of a fluorinated aryl group.

One aspect of the disclosure, therefore, provides methods of introducing a fluorine atom onto an electrophilic carbon atom, comprising mixing an insoluble basic silver salt, an organic molecule containing a leaving group, an aqueous solution of hydrofluoric acid, and a polar solvent:water composition; incubating said mixture at a temperature of about 20° C. to about 35° C., thereby obtaining a fluorinated organic product.

In one embodiment of this aspect of the disclosure, the hydrofluoric acid may comprise the isotope $^{18}$F and the fluorinated compound is a radiolabeled organic product In embodiments of the methods of the disclosure, the leaving group may be selected from the group consisting of: a chloride, a bromide, an iodide, an aryl group, an alkyl substituted sulfonate ester, an aryl substituted carboxylate ester, an alkyl substituted carboxylate ester, a nitro group, and an isothiocyanate.

In one embodiment of the disclosure, therefore, is a method of introducing a fluorine atom into a brominated aromatic ring, comprising mixing silver oxide, an aromatic ring compound, an aqueous solution of hydrofluoric acid, and a polar solvent:water composition; incubating said mixture at a temperature of about 20° C. to about 35° C., thereby obtaining a fluorinated aromatic ring compound product.

In one embodiment of this aspect of the disclosure, the molar ratio of the silver oxide:hydrofluoric acid may be from about 5:1 to about 60:1.

In another embodiment of the disclosure, the electrophile may have a concentration from about 65 mM to about 600 mM.

In yet another embodiment of the method of the disclosure, the hydrofluoric acid has a concentration from about 0.5 mM to about 10 mM.

Another aspect of the disclosure provides compositions comprising an insoluble basic silver salt and silver fluoride, wherein the silver fluoride can be disposed on a surface of the insoluble basic silver salt.

In one embodiment of this aspect of the disclosure, the insoluble basic silver salt is silver oxide or silver carbonate.

In another embodiment, the composition may result from the interaction of a $^{18}F$-radiolabeled hydrofluoric acid at the concentrations encountered as the product of a cyclotron, comprising silver fluoride $Ag^{18}F$ and silver oxide, wherein the silver fluoride is disposed on the surface of the silver oxide.

DETAILED DESCRIPTION

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

In describing and claiming the disclosed subject matter, the following terminology will be used in accordance with the definitions set forth below.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

The term "aryl" as used herein refers, unless otherwise stated, to a polyunsaturated, typically aromatic, hydrocarbon substituent which can be a single ring or multiple rings (up to three rings) which are fused together or linked covalently. The term "heteroaryl" as used herein refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include, but are not limited to, phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, purinyl, 2-benzimidazolyl, 5-indolyl, 1H-indazole, carbazole, β-carboline, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl.

The term "aryl" as used herein can refer to a phenyl or naphthyl group which is unsubstituted or substituted. The term "heteroaryl" may refer to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinoxalinyl, quinolyl or quinolyl group which is unsubstituted or substituted.

The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "aryl" and "heteroaryl") is meant to include both substituted and unsubstituted forms of the indicated radical, unless otherwise indicated Similarly, substituents for the aryl and heteroaryl groups are varied and can be selected from, but not limited to, such as: -halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$).dbd.NH, —NR'C(NH$_2$).=NH, —NH—C(NH$_2$).=NR', —S(O)R', —S(O)$_2$R', —S(O)$_2$NR'R'', —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R'' and R''' are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_2$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

The term "alkyl" as used herein refers to saturated monovalent hydrocarbon groups having straight, branched, or cyclic moieties (including fused and bridged bicyclic and spirocyclic moieties), or a combination of the foregoing moieties. For an alkyl group to have cyclic moieties, the group must have at least three carbon atoms.

The term "leaving group" as used herein refers to any group that activates the carbon bearing center towards nucleophilic attack, which is defined as an electrophile. Suitable "leaving groups" for use in the methods of the present disclosure include, but are not limited to, chloride, bromide, iodide, an aryl or alkyl substituted sulfonate ester, an aryl or alkyl substituted carboxylate ester, nitro group, or isothiocyanate.

Description

The present disclosure encompasses a general method that uses aqueous fluoride (in particular HF) to generate C—F bonds under mild conditions. The disclosure provides methods whereby aqueous fluoride can be used directly to functionalize or label molecules (Finkelstein, H. (1910) Ber. Dtsch. Chem. Ges., 43: 1528), thus offering not only a more efficient process (where no fixing is required), but can also be extended to label large macro(bio)molecules that would not be tolerant of organic solvents or more harsh reaction conditions.

Aqueous methods of the disclosure would be particularly advantageous for labeling of molecules with $^{18}$F because this isotope is generated in the cyclotron and dispensed as a solution of H[$^{18}$F] in water. The fluoride ion typically is then "fixed" and turned into nucleophilic source such as Cs[$^{18}$F] or [K/2.2.2 cryptofix][$^{18}$F]. Fluoride needs to be fixed since it is a very poor nucleophile and even trace amounts of water significantly attenuate its nucleophilicity, thereby making it unreactive.

There have been few recorded examples of nucleophilic fluorination in aqueous solvents. One possible reaction that had looked promising was the use of AgF in moist acetonitrile to displace alkyl bromides and iodides (Tannhauser et al., J. Am. Chem. Soc. (1956) 78: 2658-2659; Pogany et al., Synthesis (1987) 718). Unlike its halide congeners, silver fluoride is readily soluble in water and somewhat soluble in acetonitrile and methanol. This difference in halide solubility has been exploited to make use of AgF for nucleophilic displacements of heavier halogens from carbon centers (Finkelstein, H. Ber. Dtsch. Chem. Ges. (1910) 43: 1528). Despite fluoride's nucleophilicity in water being greatly diminished due to its tight hydration sphere, treatment of 21-iodo-progesterone derivatives with AgF in moist MeCN afforded the desired 21-F derivatives in good yield. The precipitation of AgI was observed within seconds of mixing the reagents together. Also, AgF is superior over many other fluoride sources in effecting displacement of an α-bromide in methyl stearate (Pogany et al., Synthesis (1987) 718). When methyl α-bromo stearate was exposed to TBAF, CsF, RbF, or KF+18-crown-6, the conversion yield was only 10-15% and existed as a 1:1 mixture of α-fluoro and the eliminated product.

Switching to AgF in anhydrous acetonitrile and refluxing for 24 hours also produced the same 50:50 mixture of α-fluoro to eliminated products. However, adding a small amount of water to the reaction afforded the desired product in high yield with no evidence of elimination.

Initially, a screening of fluorophilic salts that would form "MF" in situ was conducted by adding HF to their oxides or carbonates. Since $^{18}$F is dispensed as a highly dilute solution of HF in water, initial experiments used $HF_{(aq)}$ as the fluoride source.

Suspending mercuric oxide, silica gel, and barium carbonate with benzyl bromide and HF in a 3:2 solution of acetone/water resulted in no reaction and full recovery of starting material, as shown in Table 1, Example 1. However, using the insoluble silver carbonate and silver oxide afforded modest conversion (10% based on fluoride) to the desired product and a mixture of starting material and benzyl alcohol. Using the soluble silver nitrate only afforded benzyl alcohol and starting material.

Silver oxide was selected, since less starting material was consumed in the reaction then with silver carbonate. The dependency of the reaction on the solvent and fluoride source was tested, as shown in Table 2, Example 2. Converting to THF or methyl cyanide with only 10% water (originating from the HF solution) gave no reaction. Sodium fluoride, or directly adding silver fluoride, likewise gave no reaction. The reagent concentrations were also optimized, as shown in Table 3, Example 3.

The quantity of silver oxide plays an important role in the reaction. Holding the concentration of benzyl bromide at 72 mM, 50 equiv of silver oxide (relative to fluoride) provided the highest yield of benzyl fluoride at 38%. Higher quantities of silver oxide correlated to higher consumption of starting material to form benzyl fluoride and benzyl alcohol. The concentration of HF was insignificant to the yield of benzyl fluoride when varied between 7 mM and 3.5 mM, but appreciable decreases in yield were observed when the concentration of HF was dropped below 1 mM and the concentration of benzyl bromide was held constant at 72 mM. However, on increasing the concentration of benzyl bromide to 600 mM, even lowering the concentration of HF to 0.84 mM resulted in a quantitative conversion to the desire benzyl fluoride within 45 minutes.

Exposing 1 mCi of no-carrier-added $^{18}$F in water (aqueous H[$^{18}$F] directly from a cyclotron) to a 600 mM solution of benzyl bromide and 181 mM silver oxide in acetone (final ratio 3:2 acetone/water) at room temperature yielded the desired radiochemically labeled product at a 46% yield in 45 min. While not wishing to be held to any one theory, there are two factors to consider when evaluating this yield. First, the yield was based on radio-thin layer chromatography (radio-TLC), which compared the baseline $^{18}$F fluoride (presumably inorganic [$^{18}$F—]) spot to the radioactivity of the product (benzyl[$^{18}$F]fluoride) spot. Benzyl fluoride is volatile (bp=150° C.) and complete evaporation off the chromatographic plate could occur after 10 minutes, thereby reducing the apparent yield. Second, the measured yield assumed that all of the [$^{18}$F—] was free in solution, and thus transferred to the TLC plate. However, fluoride-18 may also be bound to the silver oxide support. Thus the estimated yield probably had significant error. Significantly, however, C—$^{18}$F bonds could be formed at room temperature in water in under an hour.

Without wishing to be bound by any one theory, a mechanism for the reaction may comprise as the first step, HF being absorbed onto the silver oxide surface, creating an "AgF" species attached to an underlying silver oxide matrix. This may then be followed by absorption of benzyl bromide onto the solid support, followed by fluoride displacement, precipitation of silver bromide, and then desorption of benzyl fluoride back into solution.

Two pieces of evidence support this mechanism. First, the reaction does not work when silver fluoride is used, supporting that a soluble silver fluoride is not formed when HF and silver oxide are mixed. Second, basic fluoride (NaF) does not promote the reaction. This eliminates a possible mechanism where silver oxide acts as a Lewis acid followed by nucleophilic attack of aqueous fluoride at the activated carbon center.

The methods of the disclosure therefore provide for the making of C—F bonds using anionic fluoride under mild conditions that would be advantageous for radiochemical synthesis. In the methods of the disclosure, one reaction uses silver oxide and $HF_{(aq)}$ to make benzyl fluoride from benzyl bromide. This reaction further translates to the radiochemical arena and the conversion to benzyl [$^{18}$F]fluoride.

It is contemplated, however, that the methods of the disclosure may be used for the fluorination of organic compounds, and in particular aryl organic compounds other than just benzyl halogens. It is considered, therefore, within the scope of the present disclosure, for organic compounds comprising an electrophilic carbon atom and a halogen leaving group to be fluorinated by the methods of the disclosure.

One aspect of the disclosure, therefore, provides methods of introducing a fluorine atom onto an electrophilic carbon atom, comprising mixing an insoluble basic silver salt, an organic molecule containing a leaving group, an aqueous solution of hydrofluoric acid, and a polar solvent:water composition; incubating said mixture at a temperature of about 20° C. to about 35° C., thereby obtaining a fluorinated organic product.

In one embodiment of this aspect of the disclosure, the hydrofluoric acid may comprise the isotope $^{18}$F and the fluorinated compound is a radiolabeled organic product In embodiments of the methods of the disclosure, the leaving group may be selected from the group consisting of: a chloride, a bromide, an iodide, an aryl group, an alkyl substituted sulfonate ester, an aryl substituted carboxylate ester, an alkyl substituted carboxylate ester, a nitro group, and an isothiocyanate.

In one embodiment of the disclosure, therefore, is a method of introducing a fluorine atom into a brominated aromatic ring, comprising mixing silver oxide, an aromatic ring compound, an aqueous solution of hydrofluoric acid, and a polar solvent:water composition; incubating said mixture at a temperature of about 20° C. to about 35° C., thereby obtaining a fluorinated aromatic ring compound product.

In one embodiment of this aspect of the disclosure, the molar ratio of the silver oxide:hydrofluoric acid may be from about 5:1 to about 60:1.

In another embodiment of the disclosure, the electrophile may have a concentration from about 65 mM to about 600 mM.

In yet another embodiment of the method of the disclosure, the hydrofluoric acid has a concentration from about 0.5 mM to about 10 mM.

Another aspect of the disclosure provides compositions comprising an insoluble basic silver salt and silver fluoride, wherein the silver fluoride can be disposed on a surface of the insoluble basic silver salt.

In one embodiment of this aspect of the disclosure, the insoluble basic silver salt is silver oxide or silver carbonate.

In another embodiment, the composition may result from the interaction of a $^{18}$F-radiolabeled hydrofluoric acid at the concentrations encountered as the product of a cyclotron, comprising silver fluoride Ag$^{18}$F and silver oxide, wherein the silver fluoride is disposed on the surface of the silver oxide.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

TABLE 1

Screening of metal salts to promote fluoride displacement of benzyl bromide under aqueous conditions.

| BnBr | Salt (5 equiv) | HF (conc) | Time | BnF$^a$ | BnOH$^b$ | BnBr$^b$ |
|---|---|---|---|---|---|---|
| 72 mM | HgO | 7 mM | 45 min | 0 | 0 | 100% |
| 72 mM | SiO$_2$ | 7 mM | 45 min | 0 | 0 | 100% |
| 72 mM | BaCO$_3$ | 7 mM | 45 min | 0 | 0 | 100% |
| 72 mM | Ag$_2$CO$_3$ | 7 mM | 45 min | 13% | 48% | 52% |
| 72 mM | Ag$_2$O | 7 mM | 45 min | 13% | 38% | 62% |
| 72 mM | AgNO$_3$ | 7 mM | 45 min | 0 | 35% | 65% |

Reaction conditions: Suspended salt in H$_2$O. Added HF$_{(aq)}$, and then added BnBr in acetone. Final solvent was 3:2 acetone water (5 mL). Stirred in a sealed plastic vial.
$^a$Yield based on GC/MS with internal standard (PhOMe) and relative to fluoride.
$^b$Conversion based on relative GC peak integration Example 2

TABLE 2

Effect of solvent and fluoride source on conversion of benzyl bromide to benzyl fluoride.

| BnBr | Ag$_2$O | HF | Solvent | time | BnF$^a$ | BnOH$^b$ | BnBr$^b$ |
|---|---|---|---|---|---|---|---|
| 72 mM | 36 mM | 7 mM | 3:2 acetone/water | 45 min | 13% | 38% | 62% |
| 72 mM | 36 mM | 0 | 3:2 acetone/water | 45 min | 0 | 0 | 100% |
| 72 mM | 36 mM | 7 mM | THF$^c$ | 45 min | 0 | 0 | 100% |
| 72 mM | 36 mM | 7 mM | MeCN$^c$ | 45 min | 0 | 0 | 100% |
| 72 mM | 36 mM | 7 mM (NaF) | 3:2 acetone/water | 45 min | 0 | 0 | 100% |
| 72 mM | — | 7 mM (AgF) | 1:1 H$_2$O/MeCN | 45 min | 0 | 0 | 100% |

Example 3

TABLE 3

Effect of concentration on conversion of benzyl bromide to benzyl fluoride.

| BnBr (conc) | Ag$_2$O (equiv)(conc) | HF (conc) | Time | BnF$^a$ | BnOH$^b$ | BnBr$^b$ |
|---|---|---|---|---|---|---|
| 72 mM | 1 (7 mM) | 7 mM | 45 min | 0 | 0 | 100% |
| 72 mM | 10 (36 mM) | 7 mM | 45 min | 13% | 38% | 62% |
| 72 mM | 20 (36 mM) | 3.5 mM | 45 min | 12% | 24% | 76% |
| 72 mM | 20 (72 mM) | 7 mM | 45 min | 23% | 69% | 31% |
| 72 mM | 40 (72 mM) | 3.5 mM | 45 min | 26% | 51% | 49% |
| 72 mM | 50 (181 mM) | 7 mM | 45 min | 34% | 97% | 3% |
| 72 mM | 100 (181 mM) | 3.5 mM | 45 min | 38% | 60% | 40% |
| 72 mM | 200 (181 mM) | 1.75 mM | 45 min | 10% | 100% | 0 |
| 72 mM | 400 (181 mM) | 0.875 mM | 45 min | 11% | 91% | 9% |
| 72 mM | 75 (270 mM) | 3.5 mM | 45 min | 31% | 96% | 4% |
| 72 mM | 100 (362 mM) | 7 mM | 45 min | 32% | 100% | 0 |

TABLE 3-continued

Effect of concentration on conversion of benzyl bromide to benzyl fluoride.

| BnBr (conc) | Ag$_2$O (equiv)(conc) | HF (conc) | Time | BnF$^a$ | BnOH$^b$ | BnBr$^b$ |
|---|---|---|---|---|---|---|
| 72 mM | 200 (362 mM) | 3.5 mM | 45 min | 30% | 100% | 0 |
| 72 mM | 150 (543 mM) | 7 mM | 45 min | 33% | 100% | 0 |
| 72 mM | 200 (724 mM) | 7 mM | 45 min | 33% | 100% | 0 |
| 8 mM | 250 (210 mM) | 0.84 mM | 45 min | 0% | 17% | 83% |
| 600 mM | 210 (181 mM) | 0.84 mM | 45 min | 100% | 49% | 51% |
| 600 mM | 181 mM | 1 mCi H[$^{18}$F]$^c$ | 45 min | 46%$^d$ | N/A | N/A |

Reaction conditions: Suspended Ag$_2$O in H$_2$O. Added HF$_{(aq)}$ and then add BnBr in acetone. Final solvent was 3:2 acetone water. Stirred in a sealed plastic vial.
$^a$Yield based on GC/MS with internal std (PhOMe) and relative to fluoride.
$^b$Conversion based on relative GC peak integration.
$^c$Approx. 0.4 mM.
$^d$RCY based on quantitative radio-TLC.

We claim:

1. A method of introducing a fluorine atom onto an electrophilic carbon atom of organic compound, comprising:
    mixing an insoluble basic silver salt, an organic compound containing a leaving group, an aqueous solution of hydrofluoric acid, and a polar solvent-water composition to form a mixture; and
    incubating said mixture at a temperature of about 20° C. to about 35° C., wherein the organic compound is a brominated aromatic ring, and wherein the insoluble basic silver salts is silver oxide, thereby obtaining a fluorinated aromatic ring compound product.

2. The method of claim 1, wherein the hydrofluoric acid comprises the isotope 18F and the fluorinated compound is a radiolabeled organic product.

3. The method of claim 1, wherein the leaving group may be selected from the group consisting of: a chloride, a bromide, an iodide, an aryl group, an alkyl substituted sulfonate ester, an aryl substituted carboxylate ester, an alkyl substituted carboxylate ester, a nitro group, and an isothiocyanate.

4. The method of claim 1, wherein the insoluble basic silver salt and the hydrofluoric acid are in a molar ratio of from about 5:1 to about 60:1.

5. The method of claim 1, wherein the electrophilic carbon atom is in an organic compound having a concentration from about 65 mM to about 600 mM.

6. The method of claim 1, wherein the hydrofluoric acid has a concentration from about 0.5 mM to about 10 mM.

* * * * *